United States Patent
Lee et al.

(10) Patent No.: US 7,405,312 B2
(45) Date of Patent: Jul. 29, 2008

(54) MANUFACTURING METHOD OF HEXAFLUOROPROPYLENE OXIDE WITH HIGH YIELD

(75) Inventors: Soo Bok Lee, Daejeon (KR); In Jun Park, Daejeon (KR); Dong-Kwon Kim, Daejeon (KR); Jeong-Hoon Kim, Daejeon (KR); Jong-Wook Ha, Daejeon (KR); Bong-Jun Chang, Daejeon (KR); Kwang-won Lee, Daejeon (KR); Kwang-Han Kim, Daejeon (KR); Jaewon Kim, Seoul (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 11/702,412

(22) Filed: Feb. 5, 2007

(65) Prior Publication Data

US 2008/0091052 A1 Apr. 17, 2008

(30) Foreign Application Priority Data

Oct. 16, 2006 (KR) .................... 10-2006-0100490

(51) Int. Cl.
*C07D 301/24* (2006.01)

(52) U.S. Cl. ...................................... 549/520; 549/521
(58) Field of Classification Search ................ 549/520, 549/521
See application file for complete search history.

(56) References Cited

U.S. PATENT DOCUMENTS 4,925,961 A * 5/1990 Ikeda et al. ................. 549/521

FOREIGN PATENT DOCUMENTS

JP 58131976 * 8/1983

* cited by examiner

*Primary Examiner*—Jafar Parsa
(74) *Attorney, Agent, or Firm*—Frommer Lawrence & Haug LLP; Ronald R. Santucci

(57) ABSTRACT

The present invention relates to a method for preparing hexafluoropropylene oxide with high yield, and particularly to a method for preparing hexafluoropropylene oxide comprising the step of performing a two-phase interfacial reaction between an organic phase containing hexafluoropropylene and an aqueous phase containing a hypochlorite oxidant in the presence of a phase-transfer catalyst and a non-ionic surfactant to improve the degree of emulsification and dispersion of the organic phase and to increase the contact interfacial area, thereby increasing the efficiency and the yield of the reaction.

3 Claims, No Drawings

MANUFACTURING METHOD OF HEXAFLUOROPROPYLENE OXIDE WITH HIGH YIELD

TECHNICAL FIELD

The present invention relates to a method for preparing hexafluoropropylene oxide with high yield, and particularly to a method for preparing hexafluoropropylene oxide comprising the step of performing a two-phase interfacial reaction between an organic phase containing hexafluoropropylene and an aqueous phase containing a hypochlorite oxidant in the presence of a phase-transfer catalyst and non-ionic surfactants to improve the degree of emulsification and dispersion of the organic phase and to increase the contact interfacial area, thereby increasing the efficiency and yield of the reaction.

RELATED PRIOR ART

Hexafluoropropylene oxide ('HFPO' hereinafter) is a derivative that may be used in preparing useful fluorine compound such as hexafluoroacetone and perfluoro-vinylether. Further, HFPO polymers are widely used as heat-transfer fluids and lubricants.

HFPO is synthesized by the epoxidation of hexafluoropropylene ('HFP' hereinafter). HFP differs greatly from hydrocarbon olefins such as propylene or chlorinated hydrocarbon olefins such as allyl chloride in chemical property, and thus it may not be readily epoxidized as is the case with propylene or allyl chloride.

Propylene or allyl chloride is transformed into chlorohydrin, followed by epoxidation using a chlorohydrin method, where the ring is opened by an alkali. However, in the case of HFP, the chlorohydrin is unstable and decomposed into carbonyl compounds, thereby preventing the production of HFPO.

There have been suggested other methods for the epoxidation of HFP using hydrogen peroxide, oxygen or hypochlorite.

In the oxidation method using hypochlorite, HFPO is synthesized from HFP in the system where a water-soluble polar solvent such as acetonitrile or diglyme is added in hypochlorite aqueous solution. The selectivity of HFPO was as low as 10% in this method, because the produced HFPO reacted with water and easily decomposed into other compounds in the uniform mixture system of a water-soluble polar solvent and an alkaline hypochlorite aqueous solution.

There have been many methods to increase the conversion of HFP and the selectivity of HFPO.

Japanese patent publication No. 57-15539 discloses a method for preparing HFPO in a two-phase system consisting of an aqueous phase and containing hypochlorite and an organic phase containing HFP. The hypochlorite was used as an oxidant, and a quaternary ammonium salt or a quaternary phosphonium salt may be used as a phase-transfer catalyst. Using this method, HFPO may be prepared from HFP with a yield of 40-70% because the produced HFPO exists in the organic phase and does not decompose into other compounds. However, the conversion of HFP and the selectivity of HFPO were not sufficient.

Accordingly, the present inventors have performed extensive researches to develop a way to maximize the yield of HFPO, and as a result, completed the present invention based on the findings that HFPO can be prepared from HFP with high yield when a two-phase interfacial reaction is performed between an organic phase containing hexafluoropropylene and an aqueous phase containing a hypochlorite oxidant in the presence of a phase-transfer catalyst and non-ionic surfactants.

Therefore, an object of the present invention is to provide a process for preparing HFPO with high yield.

DETAILED DESCRIPTION OF INVENTION

The present invention relates to a method for preparing a hexafluoropropylene oxide (HFPO), which comprises the step of performing a two-phase interfacial reaction between an organic phase containing hexafluoropropylene (HFP) and an aqueous phase containing a hypochlorite oxidant in the presence of a phase-transfer catalyst, wherein the interfacial reaction is performed by using non-ionic surfactants in the amount of 0.1-5 wt % relative to the total weight of the reactant.

Hereunder is provided a detailed description of the present invention.

The present invention relates to a method for preparing hexafluoropropylene oxide (HFPO) with high yield using hexafluoropropylene (HFP) by performing a two-phase interfacial reaction in the presence of predetermined amount of phase-transfer catalyst and non-ionic surfactants.

Typically, surfactants are used to increase the rate and degree of reaction when performing an interfacial reaction. One of the technical features of the present invention lies in the utilization of the non-ionic surfactants among various surfactants such as cationic, anionic and non-ionic surfactant. The non-ionic surfactants help the hypochlorite ion to easily move from the aqueous phase to the organic phase and react with HFP dissolved in the organic phase. The non-ionic surfactants also improve the emulsification or dispersion of the organic phase and increase the contact interfacial area, thereby improving the reaction efficiency. A cationic or anionic surfactant causes 'ion trouble' with an oxidant and a phase-transfer catalyst, and may not improve the yield sufficiently.

In the present invention, HFPO is prepared by contacting the aqueous phase containing a hypochlorite oxidant with the organic phase containing HFP and using a phase-transfer catalyst and non-ionic surfactants in the interface between the two phases.

A hypochlorite used herein is decomposed into a hypochlorite ion during the reaction, and examples of the hypochlorite include alkaline metal hypochlorites such as sodium hypochlorite and potassium hypochlorite. Mass produced on an industrial scale as a bleaching agent or a sterilizer, the sodium hypochlorite and the potassium hypochlorite are cheap and appropriate for the use herein.

The concentration of the hypochlorite aqueous solution is preferred to be controlled to such a range that the effective concentration of chlorine may be 5-20 wt %. If the effective concentration of chlorine is lower than 5 wt %, it is necessary to handle a lot of water, thus decreasing economical efficiency. If the effective concentration of chlorine is higher than 20 wt %, the hypochlorite may become unstable and difficult to handle.

Hypochlorite and HFP may be used without limitation in the ratio that is generally accepted by one skilled in the art. The hypochlorite is preferred to be used in the amount of 1-10 equivalents relative to an equivalent of HFP. If the amount of the hypochlorite is less than 1 equivalent, the conversion may become too low. If the amount is greater than 10 equivalents, the economic efficiency may be lowered despite the high conversion.

Inert solvent that is immiscible with an aqueous phase may be used as the organic phase herein. Preferred examples of the organic phase include fluorine containing compounds such as chlorofluorocarbon and perfluorocarbon. Preferable examples of the chlorofluorocarbon include trichlorofluoroethane, 1,2-difluorotetrachloroethane and 1,1,2-trifluoro-1,2,2-trichloroethane, and preferable examples of the perfluorocarbon include perfluorocyclobutane, perfluorodimethylcyclobutane, perfluorohexane and perfluorooctane.

An organic phase and an aqueous phase may be used in the amount that is acceptable to one skilled in the art, and the amount may be determined based on the method or the condition of a reaction. However, the aqueous phase is preferred to be used in the volume ratio of 0.1-2 relative to that of the organic phase in the present invention. If the aqueous phase is used less than 0.1 vol %, the interfacial area and the reaction efficiency may be decreased. If the aqueous phase is used more than 2 vol %, the efficiency may be lowered during the scale-up process due to excess amount of the reactant solution.

Any conventional phase-transfer catalyst used in the manufacture of hexafluoropropylene oxide (HFPO) may also be used in the present invention. Examples of the phase-transfer catalyst include quaternary ammonium salt and quaternary phosphonium salt. Examples of the quaternary ammonium salt include tri-n-octylmethylammonium chloride and tetra-n-butylammonium chloride, and examples of the quaternary phosphonium salt include tri-n-octylmethylphosphonium chloride and tetra-n-butylphosphonium chloride.

The amount of the catalyst may be appropriately determined based on the structure of a catalyst, the kind of a solvent, the reaction temperature and the desired reaction rate. In the present invention, the catalyst may be used in the amount of 0.02-1 mole relative to one gram equivalent of hypochlorite ion. If the amount of the catalyst is less than 0.02 mole, the reaction will proceed very slowly. If the amount is higher than one mole, the reaction rate may be too high to control, thus increasing the cost leading to economic disadvantage.

Any conventional non-ionic surfactant that is utilized in the art may also be used in the present invention. Examples of the non-ionic surfactant include esters between higher fatty acid and polyethyleneglycol or diethanolamine, higher amine adducted with ethylene oxide, and higher fatty acid amides adducted with ethylene oxide. Preferably, a compound having an amine oxide and perfluoroalkyl groups ($C_nF_{2n+1}CH_2CH_2$—, n=3-21) at the ends may be used as the non-ionic surfactants.

The non-ionic surfactant may be used in the amount of 0.1-5 wt % relative to the total weight of the aqueous phase and the organic phase. If the amount is less than 0.1 wt %, an interfacial tension may not be sufficiently decreased. If the amount is greater than 5 wt %, it is necessary to treat the wastewater after reaction to the use of excessive surfactant.

The temperature and the pressure may be determined in the present invention based on the amount of the catalyst, the content of the reactant solution and the desired reaction rate. Preferably, the temperature and the pressure may are −20 to 40° C. and 1-10 atm. If the temperature is lower than −20° C., the reaction may proceed too slowly or may not proceed due to the freezing of the aqueous phase. If the temperature is higher than 40° C., the selectivity of HFPO may be lowered due to the decomposition of HFPO.

Thus produced HFPO is substantially contained in the organic phase, and may be easily separated from the organic phase by distillation. After the separation, the organic phase may be recycled for the reaction.

According to the present invention, the conversion of HFP and the selectivity of HFPO may be increased to higher than 90%, preferably 93-95%. Further, the conversion of HFPO increases to 97-99%, i.e. nearly 100%, and thus any complicated process for the separation of HFP/HFPO and the recyclization of HFP is not necessary.

EXAMPLES

The present invention is described more specifically by the following Examples. Examples herein are meant only to illustrate the present invention, but they should not be construed as limiting the scope of the claimed invention.

Example 1

54 mL of 1,1,2-trichloro-1,2,2-trifluoroethane ('R-113' hereinafter), 30 mL of aqueous solution of sodium hypochlorite (effective concentration of chlorine: 12%), 0.2 g of tri-n-octylmethylammonium chloride and 1.0 g of $R_fCONH(CH_2)_3NO(CH_3)_2$ ($R_f=C_nF_{2n+1}CH_2CH_2$—, a perfluoroalkyl group having an average carbon number of 6; non-ionic surfactant) were added in a pressure-resistant autoclave (inner volume: 100 mL) equipped with a Teflon stirrer. This was cooled down using liquid nitrogen and purged into vacuum. After 2.6 g of HFP was added, the temperature was slowly elevated and a reaction was performed at 0° C. for 2 hours.

After the termination of the reaction, the reaction solution was left without agitation, and subject to the analysis of HFP and HFPO contained in the R-113 phase using a gas chromatography. The conversion of HFP was 97% and the selectivity of HFPO was 93%.

Example 2

Experiment was performed same as in Example 1 except that 1.2 g of $C_{17}H_{25}NO(CH_3)_2$ was used as the non-ionic surfactant. The conversion of HFP was 94% and the selectivity of HFPO was 97%.

Comparative Example 1

Experiment was performed same as in Example 1 except that a non-ionic surfactant was not used. The conversion of HFP was 72% and the selectivity of HFPO was 74%.

Comparative Example 2

Experiment was performed same as in Example 1 except that $C_{18}H_{37}N(CH_3)_3Cl$ was used as a cationic surfactant instead of the non-ionic surfactant. The conversion of HFP was 65% and the selectivity of HFPO was 67%.

Comparative Example 3

Experiment was performed same as in Example 1 except that sodium dodecyl benzene sulfonate was used as an anionic surfactant instead of the non-ionic surfactant. The conversion of HFP was 71% and the selectivity of HFPO was 74%.

As shown above, Examples 1 and 2, where a non-ionic surfactant was used, showed a remarkable increase in the conversion of HFP and the selectivity of HFPO as compared to Comparative Example 1, where non-ionic surfactant was not used.

Further, according to the present invention, the use of a non-ionic surfactant along with a phase-transfer catalyst in predetermined amount greatly increase the conversion of HFP and the selectivity of HFPO, when a two-phase interfacial reaction is performed between an organic phase containing HFP and an aqueous phase containing a hypochlorite oxidant.

What is claimed is:

1. A method for preparing a hexafluoropropylene oxide, comprising the step of performing a two-phase interfacial reaction between an organic phase containing hexafluoropropylene and an aqueous phase containing a hypochlorite oxidant in the presence of a phase-transfer catalyst, wherein the interfacial reaction is performed by using a non-ionic surfactant having an amine oxide group and perfluoroalkyl group of $C_nF_{2n+1}CH_2CH_2$—, n=3–21 in the amount of 0.1-5 wt % relative to the total weight of the aqueous phase and the organic phase.

2. The method of claim 1, wherein the non-ionic surfactant is $R_fCONH(CH_2)_3NO(CH_3)_2$, wherein $R_f$ is a perfluoroalkyl group having a carbon number of 6.

3. A method for preparing a hexafluoropropylene oxide, comprising the step of performing a two-phase interfacial reaction between an organic phase containing hexafluoropropylene and an aqueous phase containing a hypochlorite oxidant in the presence of a phase-transfer catalyst, wherein the interfacial reaction is performed by using a non-ionic surfactant of $C_{17}H_{25}NO(CH_3)_2$ in the amount of 0.1-5 wt % relative to the total weight of the aqueous phase and the organic phase.

* * * * *